United States Patent [19]
Jacquault

[11] Patent Number: 5,498,857
[45] Date of Patent: Mar. 12, 1996

[54] MICROWAVE HEATING DEVICE WITH DEFLECTORS FOR SIMULTANEOUSLY TREATING PLURAL SAMPLES

[75] Inventor: Patrick Jacquault, Sevres, France

[73] Assignee: Societe Prolabo, Fontenay-Sous-Bois, France

[21] Appl. No.: 363,741

[22] Filed: Dec. 23, 1994

[30] Foreign Application Priority Data

Dec. 28, 1993 [FR] France .................................. 93 15735

[51] Int. Cl.⁶ .................................................. H05B 6/80
[52] U.S. Cl. ........................... 219/745; 219/746; 219/762; 219/687; 422/21
[58] Field of Search ..................................... 219/745, 746, 219/747, 756, 762, 728, 729, 687; 422/21, 63

[56] References Cited

U.S. PATENT DOCUMENTS

| | | | |
|---|---|---|---|
| 4,693,867 | 9/1987 | Commarmot et al. | 219/756 |
| 4,877,933 | 10/1989 | Yangas | 219/745 |
| 4,889,966 | 12/1989 | Meredith | 219/684 |
| 5,304,766 | 4/1994 | Baudet et al. | 219/687 |
| 5,308,944 | 5/1994 | Stone-Elander et al. | 219/687 |

FOREIGN PATENT DOCUMENTS 0496684  1/1992  European Pat. Off. .......... G01N 1/28

*Primary Examiner*—Philip H. Leung
*Attorney, Agent, or Firm*—Blakely, Sokoloff, Taylor & Zafman

[57] ABSTRACT

The invention relates to a device for simultaneous treatment in a wet medium of four samples contained in four flasks placed in a microwave application cavity, four microwave deflectors being placed inside the application cavity. According to the invention, each deflector is formed by a cylindrical surface that surrounds a fraction of the outside surface of the flask, which fraction lies in the range one-fourth to one-half and the deflectors are symmetrically disposed in pairs about the axis X of the application cavity, and they are disposed for the most part on opposite sides of planes containing the axis X and the two axes of the corresponding flasks, the concave sides of the four deflectors facing in alternating directions.

12 Claims, 1 Drawing Sheet

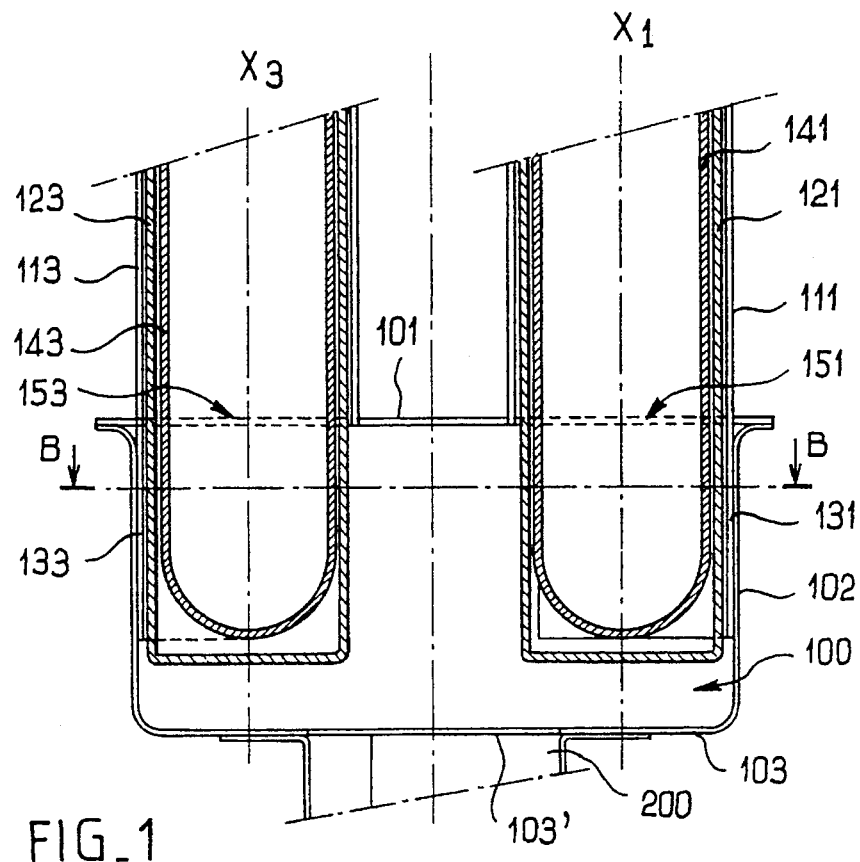
FIG_1
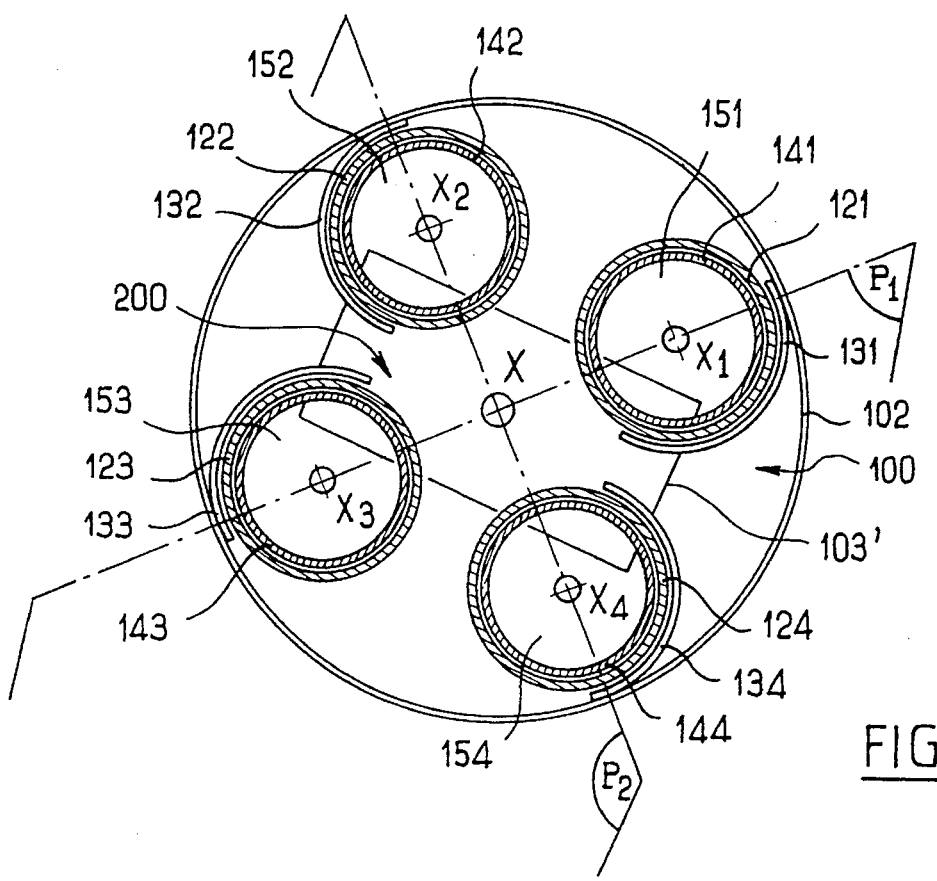
FIG_2

MICROWAVE HEATING DEVICE WITH DEFLECTORS FOR SIMULTANEOUSLY TREATING PLURAL SAMPLES

The present invention relates to apparatus for simultaneously treating a plurality of samples in a wet medium, the device making use of microwave heating of the samples.

A particularly advantageous application of the invention lies in its use for making various extraction products by microwave heating of specific compounds, such as the extraction of pollutants from sediments, for example.

BACKGROUND OF THE INVENTION

The invention relates to an improvement of the device described in French patent application FR-2 681 431 in the name of the Applicant, which device includes means for emitting microwaves into a cylindrically-shaped application cavity where the microwaves are applied.

More particularly, the application cavity has a central axis of symmetry X and in its top wall it includes four cylindrical wells that open out to the inside of the cavity via circular openings. Test tubes or flasks containing samples are inserted into the microwave application cavity via the openings. In addition, the application cavity includes deflectors for the purpose of distributing microwaves better inside the cavity. The deflectors are made of materials that are not permeable to microwaves.

In a first embodiment of the device described in the above-specified French patent application, the deflectors are substantially plane and rectangular, the axis X of the application cavity being situated in the planes thereof, the deflectors being disposed radially and being regularly distributed between the flasks.

In a second embodiment, the deflectors are constituted by cylindrical surfaces having generator lines parallel to the axis X of the cavity, and they are secured to the side wall of the application cavity. They are disposed symmetrically about a plane of symmetry containing the axis X of the cavity and the axis Y of the waveguide perpendicular to said axis X so that on a given side of the plane of symmetry said deflectors are disposed in such a manner that the concave face of one deflector faces the convex face of an adjacent deflector. The concave faces of the deflectors face towards the opening of the waveguide in the side wall of the application cavity.

In a third embodiment, each of the deflectors is constituted by a cylindrical wall having generator lines parallel to the axis X of the application cavity, said cylindrical wall substantially surrounding each flask and being open towards the center of the cavity. Pairs of adjacent deflectors are interconnected by respective link walls. The space extending between the deflectors and the link walls, and the side wall of the application cavity is preferably filled with a material that is impermeable to microwaves, and that is preferably a thermal insulator.

When that device is in use, it turns out that none of the above-specified dispositions of the deflectors is satisfactory.

In particular, those embodiments do not enable the electric field of the microwaves to be distributed uniformly throughout the entire cavity, so the field is concentrated at certain special points on the surfaces of the flasks, which points are referred to as "impact points". The flasks are generally made of glass and as a result the impact points give rise to melting and/or cracking phenomena in the glass, thereby damaging the flasks.

In addition, the last-mentioned particular disposition of the deflectors is complex and too expensive for mass production of such a device.

OBJECTS AND SUMMARY OF THE INVENTION

In order to mitigate the above drawbacks, the invention proposes a device in which the shape and the positioning of the deflectors in the microwave application cavity is optimized so as to protect the surface zones of the flasks that are exposed to impacts, while nevertheless being simple and easy to implement.

More particularly, the invention provides an apparatus for simultaneously treating in a wet medium four samples contained in four flasks having respective axes $X_1$, $X_2$, $X_3$, and $X_4$, the device comprising firstly means for emitting microwaves inside an application cavity having a central axis of symmetry X, the top wall of the application cavity including four openings through which the flasks are inserted parallel to the axis X into the inside of said cavity, the openings being disposed in symmetrical opposite pairs about the axis X, and also four microwave deflectors placed inside the application cavity. In the device each deflector is formed by a cylindrical surface that surrounds a fraction of the outside surface of a flask where said fraction lies between one-fourth and one-half thereof, and the deflectors are disposed symmetrically in pairs about the axis X and are for the most part disposed on opposite sides of a plane containing the axis X and the two axes of the corresponding flasks, the concave sides of the four deflectors facing in alternating directions.

BRIEF DESCRIPTION OF THE DRAWINGS

The following description made with reference to the accompanying drawings is given by way of non-limiting example and shows what the invention consists of and how it can be performed.

FIG. 1 is a section view through the microwave application cavity of a device of the invention.

FIG. 2 is a section view on plane B—B through the cavity of FIG. 1.

MORE DETAILED DESCRIPTION

FIGS. 1 and 2 show a microwave application cavity 100 that forms part of a device for applying treatment in a wet medium simultaneously to four samples contained in four flasks, the device using microwave heating of the samples. Such a device is described overall both structurally and functionally in French patent application FR-2 681 431 belonging to the Applicant. Consequently, the device is not described again herein overall and the present detailed description relates only to a particular embodiment of the improved application cavity.

The application cavity 100 is represented herein as being cylindrical in shape about a central axis of symmetry X, and it comprises a top wall 101, a side wall 102, and a bottom wall 103. The bottom wall 103 of the application cavity 100 includes a rectangular window 103' that is transparent to microwaves and through which a waveguide 200 perpendicular to the bottom wall 103 opens out into the inside of said cavity. The waveguide 200 is connected to a microwave generator (not shown herein) and it conveys microwaves to the application cavity.

As can be seen better in FIG. 1, the axis of the waveguide 200 corresponds to the axis of symmetry X of the cavity. The top wall 101 of the application cavity 100 includes four circular openings 151, 152, 153, and 154 disposed in pairs that are symmetrically opposite about the axis X and in such a manner that the centers of said openings are positioned in pairs on opposite sides of the window 103' along the long sides thereof. In addition, the application cavity 100 carries four identical wells outside its top wall 101 (two of the wells being shown herein). Each cylindrical well 111, 113 extends towards the outside of the cavity perpendicularly to the top wall 101 starting from each circular orifice 151, 153 provided through said top wall 101. The section of each well 111, 113 corresponds to the section of each opening 151, 153, and the depth of each well is such as to form a barrier to the absorption of microwaves for the purpose of avoiding microwave propagation towards the outside of the application cavity. The vertical axes $X_1$, $X_2$, $X_3$, and $X_4$ of the cylindrical walls are parallel to the axis X, and they pass through the centers of the openings 151, 152, 153, and 154.

In addition, the samples to be treated (not shown herein) are contained in four glass flasks 141, 142, 143, and 144. The flasks 141, 142, 143, 144 are themselves positioned in protective cylindrical glove fingers 121, 122, 123, 124 made of a material that is permeable to microwaves. The section of each glass finger is such that the cylindrical outside surface of each flask is positioned against the cylindrical inside surface of each glove finger. Each assembly of associated flasks and glove finger is inserted vertically into each well towards the application cavity 100 via the openings 151, 152, 153, 154 in such a manner that a portion of each flask is immersed in said cavity. When the flasks and the glove fingers are positioned in the wells, the axes $X_1$, $X_2$, $X_3$, and $X_4$ of the wells correspond to the axes of said flasks.

It should be specified that the height of each flask in the application cavity 100 above the bottom wall 103 is determined experimentally so as to obtain the best time for mineralizing the samples. Naturally samples (not shown herein) are placed in those portions of the flasks that are immersed in the cavity. Furthermore, the flasks are situated at a certain distance away from the ends of the glove fingers. This distance is likewise determined experimentally as a function of the time required for mineralizing the samples.

Furthermore, as can be seen more clearly in FIG. 2, four identical deflectors 131, 132, 133, 134 are placed inside the application cavity 100. The deflectors 131, 132, 133, 134 are made of a reflecting material that is not permeable to microwaves, e.g. a metal. Each deflector 131, 132, 133, 134 is made of a cylindrical surface placed in this case against the cylindrical outside surface of each glove finger 121, 122, 123, 124 in such a manner as to surround a fraction of the outside surface of each flask 141, 142, 143, 144, where the fraction lies in the range one-fourth to one-half. In this disposition there is practically no empty space between each deflector and each surrounded flask surface portion. Each deflector is concentric with each associated glove finger and each associated flask. The deflectors are disposed symmetrically in pairs that are opposite about the axis X. In addition, each symmetrically opposite pair of deflectors is disposed for the most part on opposite sides of a plane containing the axis X and the axes of the two corresponding flasks. The four positioned deflectors are concave in alternating directions. More precisely, the two deflectors 131 and 133 that are symmetrical about the axis X are placed for the most part on opposite sides of the plane $P_1$ containing the axis X and the axes $X_1$ and $X_3$ of the flasks 141 and 143. The two deflectors 132 and 134 that are symmetrical about the axis X are positioned for the most part on opposite sides of the plane $P_2$ that contains the axis X and the axes $X_2$ and $X_4$ of the flasks 142 and 144. The planes $P_1$ and $P_2$ are mutually perpendicular.

The term "for the most part" means, as shown in FIG. 2, practically the entire length of each deflector is situated on a particular side of one of the planes $P_1$ or $P_2$.

It should be specified that each deflector 131, 132, 133, 134 is positioned in such a manner as to include an end portion which extends above a corner region of the area of the rectangular window 103'. In the embodiment shown, each deflector 131, 132, 133, 134 projects over one of the short sides of the window 103' close to a midline (not shown herein) of the rectangular window 103'.

As shown more clearly in FIG. 1, each deflector 131, 133 extends over the entire height of the corresponding flask 141, 143 that is to be found inside the application cavity 100. Thus, the disposition of the deflectors is determined experimentally to surround and thus protect the surface areas of the flasks and of the glove fingers that would otherwise be exposed to impacts due to a concentration of the microwave electric field inside the cavity, while still enabling the samples to be heated sufficiently to obtain mineralization in acceptable time.

It should be specified that in the embodiment shown, each deflector is integrally formed with each well and constitutes an extension of a portion of the cylindrical wall of the well into the inside of the application cavity.

In another embodiment (not shown herein), it is possible to envisage each deflector constituting an independent part bonded to the top wall of the application cavity in the immediate vicinity of each associated glove finger and flask, and thus close to the edge of each opening in the top wall of the cavity.

In this embodiment, it can happen that each deflector is not placed against the outside surface of the corresponding glove finger. Under such circumstances, the distance between each deflector and each glove finger is determined experimentally so that there is no risk of impact on the flask.

I claim:

1. A microwave device for simultaneously treating in a wet medium a plurality of samples in a plurality of flasks, wherein each sample is contained in a respective flask, each flask having a length, an axis, and an outside surface, the device comprising:

a) an application cavity having a central axis of symmetry (X), said application cavity further including
   i) a top wall, the top wall of the application cavity including a plurality of openings, the openings being disposed in symmetrical opposite pairs about the central axis of symmetry (X),
   ii) a plurality of support means disposed in the application cavity for supporting the flasks, wherein each flask is received into a respective support means through a respective opening, and
   iii) a plurality of deflectors disposed inside the application cavity for evenly distributing microwaves in the application cavity, wherein each deflector is formed by a cylindrical body that surrounds a fraction of the outside surface of the respective flask, said cylindrical body having a concave surface, and wherein the deflectors are disposed symmetrically in pairs about the central axis of symmetry (X) and wherein a substantial portion of the deflectors are disposed on opposite sides of a plane containing the central axis of symmetry and the two axes of the corresponding flasks, wherein the concave surfaces of the deflectors of each pair are opposed to each other, and b) means coupled to the application cavity for emitting microwaves into the application cavity.

2. The device according to claim 1, wherein each deflector extends over the entire length of the flask.

3. The device according to claim 1, wherein each deflector is disposed adjacent to the respective flask.

4. The device according to claim 1, wherein the supports means are protective glove fingers made of a material that is permeable to microwaves, each of said glove fingers having an outer surface, wherein each glove finger is adapted to support a respective flask, said flask being received into the application cavity via the corresponding opening in the top wall, wherein each deflector surrounds a fraction of the outside surface of the corresponding glove finger.

5. A device according to claim 1, wherein each opening includes a through section, and wherein each opening in the top wall of the application cavity is provided with a well that is cylindrical in shape, wherein said well extends towards the outside of the cavity and includes a section equal to the through section of said opening, said well forming a microwave absorption barrier, wherein each deflector is integrally formed with each well and constitutes an extension towards the inside of the application cavity of a fraction of the cylindrical side wall of each well.

6. The device according to claim 1, wherein each deflector is bonded to the top of the top wall of the application cavity adjacent to each opening.

7. The device according to claim 1, wherein each deflector is concentric with each flask.

8. A device according to claim 1, wherein the openings are circular, and further comprising a window disposed in a bottom wall of the application cavity, said window being transparent to microwaves whereby microwaves are emitted into the application cavity through the window, wherein the openings of said application cavity are positioned in pairs on opposite sides of the window along the long sides thereof, and each of said deflectors includes an end portion which extends over a portion of said window.

9. The microwave device as set forth in claim 1, wherein the means for emitting microwaves includes a microwave generator for generating microwaves and a waveguide coupled to the microwave generator, for directing microwaves into the application cavity.

10. The microwave device as set forth in claim 1, wherein said fraction is between one-fourth and one-half.

11. The microwave device as set forth in claim 1, wherein the deflectors are made of a reflecting material, said material not permeable to microwaves.

12. The microwave device as set forth in claim 1, wherein each flask is inserted parallel to the central axis of symmetry via a respective opening into the application cavity, and wherein the support means are provided inside each of the openings for supporting the flask.

* * * * *